(12) United States Patent
Arlt

(10) Patent No.: US 7,109,344 B2
(45) Date of Patent: Sep. 19, 2006

(54) RUTHENIUM CATALYST

(75) Inventor: Dieter Arlt, Lemgo (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 189 days.

(21) Appl. No.: 11/004,113

(22) Filed: Dec. 3, 2004

(65) Prior Publication Data
US 2005/0143580 A1    Jun. 30, 2005

Related U.S. Application Data

(60) Provisional application No. 60/531,774, filed on Dec. 22, 2003.

(30) Foreign Application Priority Data
Dec. 4, 2003   (EP) ................... 03027828

(51) Int. Cl.
C07F 15/00 (2006.01)
C07F 9/02 (2006.01)
B01J 31/00 (2006.01)

(52) U.S. Cl. ............... 548/101; 548/262.2; 556/21; 556/22; 556/136; 502/152; 502/162; 502/167

(58) Field of Classification Search ........... 548/101, 548/262.2; 556/21, 22, 136; 502/152, 162, 502/167; 585/457, 645, 358
See application file for complete search history.

(56) References Cited

U.S. PATENT DOCUMENTS

| 6,306,987 B1 * | 10/2001 | Van Der Schaaf et al. . 526/171 |
| 6,613,910 B1 * | 9/2003 | Grubbs et al. ............... 548/103 |
| 6,620,955 B1 * | 9/2003 | Pederson et al. ............. 556/21 |
| 6,867,303 B1 * | 3/2005 | Grela .......................... 548/101 |
| 6,884,859 B1 * | 4/2005 | Grubbs et al. ............... 526/135 |

2004/0087438 A1 * 5/2004 Blechert et al. ............ 502/159

OTHER PUBLICATIONS

Grela, Karol, et al., "A highly efficient ruthenium catalyst for methathesis reactions", Agnew. Chem. Int. Ed., vol. 41, No. 21, 2002; pp. 4038-4040.
Wakamatsu, Hideaki, et al., "A new highly efficient ruthenium methathesis catalyst", Agnew. Chem., vol. 114, No. 13, 2002, pp. 2509-2511.
Garber, Steven B. et al., "Efficient and Recyclable Monomeric and Dendritic Ru-Based Metathesis Catalysts", J. Am. Chem. Soc., vol. 122, 2000, pp. 8168-8179.
Zaja, Mirko, et al., "Ruthenium Olefin Metathesis Catalysts with Modified Styrene ethers: Influence of Steric and Electronic Effects", Tetrahedron, vol. 59, No. 34, 2003, pp. 6545-6558.

* cited by examiner

*Primary Examiner*—Porfirio Nazario-Gonzalez
(74) *Attorney, Agent, or Firm*—Michael P. Morris; Philip I. Datlow; Mary Ellen M. Devlin (57) ABSTRACT

The invention relates to new (pre)catalysts of ruthenium complexes of formula 1,

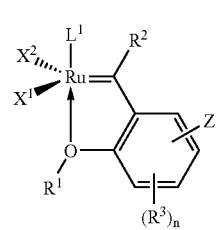

wherein $L^1$, $X^1$, $X^{\prime 2}$, $R^1$, $R^2$, $R^3$, Z and n are as defined in claim 1. The novel ruthenium complexes of formula 1 are convenient (pre)catalysts for metathesis reactions and can be applied i.e. for ring-closing metathesis, cross metathesis or ene-ine metathesis reactions.

21 Claims, 1 Drawing Sheet

Figure 1

RUTHENIUM CATALYST

RELATED APPLICATIONS

This application claims benefit from U.S. Provisional Application No. 60/531,774, filed Dec. 22, 2003.

TECHNICAL FIELD

This invention relates to ruthenium carbene complexes of formula 1, their synthesis and their practical use as catalysts for different types of metathesis reactions.

1

BACKGROUND INFORMATION

Great progress has been made in the last few years in the application of olefins metathesis in organic synthesis. Some ruthenium carbene complexes acting as (pre)catalysts have been developed, which possess a high activity in various metathesis reactions as well as a broad tolerance for a number of functional groups. This combination of characteristics is a basis for the usability of such (pre)catalysts in organic synthesis.

Moreover, for the practical application, especially in industrial scale, it is very desirable that these ruthenium complexes are stable for a longer period of time in the conditions of thermal load and that they can be stored, purified and applied without the atmosphere of protective gases.

Ruthenium complexes with the above mentioned characteristics are known in literature. See J. Am. Chem. Soc. 2000, 122, 8168–8179 or Tetrahedron Lett. 2000, 41, 9973–9976.

However, it has been discovered that a better stability is connected with a lower catalytic activity. Such a limitation was found for example for the (pre)catalyst of the formula A (see *Angew. Chemie Int. Ed.* 2002, 114, 832).

A

B

C

Next, (pre)catalysts of the formula B and C were described, which demonstrate a higher catalytic activity in comparison with the (pre)catalyst of the formula A. The catalysts A, B and C contain an iso-propoxy group chelating the metal atom. The reason for a higher activity of the systems B and C is a steric hindrance caused by the presence of a phenyl or a (substituted) naphthyl group in ortho-position to the iso-propoxy group (*Angew. Chemie Int. Ed.* 2002, 114, 832; *Angew. Chemie Int. Ed.* 2002, 114, 2509).

It has been found surprisingly that ruthenium complex (pre)catalysts of general formula 1, demonstrate much higher catalytic activity in comparison to known highly active ruthenium complexes and that these complexes are at the same time thermal and air stable.

SUMMARY OF THE INVENTION

The present invention relates to novel ruthenium complexes of formula 1, their synthesis, the synthesis of all intermediates and the use of complexes of formula 1 as catalysts or as precatalysts,

1 wherein:

$X^1$ and $X^2$ are anionic ligands;

$L^1$ is a neutral ligand;

$R^1$ is $-C_{1-20}$-alkyl, $-C_{1-20}$-haloalkyl, $-C_{3-8}$-cycloalkyl or $-C_{7-13}$-aralkyl;

$R^2$ is H, $-C_{1-20}$-alkyl, $-C_{2-20}$-alkenyl, $-C_{2-20}$-alkynyl or aryl;

$R^3$ is $-C_{1-6}$alkyl, $-C_{1-6}$-alkoxy, aryl, F or Cl;

n is 0, 1, 2 or 3;

Z is $-CO-R^4$, $-SO_2-R^5$ or $-PO(R^6)_2$;

$R^4$ is $-C_{1-20}$-alkyl or $-C_{3-8}$-cycloalkyl, both optionally substituted by one or more group selected from each independently F, Cl, Br, I or $-C_{1-6}$-alkoxycarbonyl, or aryl or heteroaryl both optionally substituted by one or more group selected from each independently F, Cl, Br, I, $-C_{1-6}$-alkyl, $-C_{1-6}$-alkoxy, $-NO_2$, $-CN$, $-CF_3$, $-OCF_3$ or $-C_{1-6}$alkoxycarbonyl $R^5$ is $-C_{1-8}$-fluoroalkyl, aryl or heteroaryl, wherein aryl or heteroaryl are both optionally substituted by one or more groups selected from each independently F, Cl, Br, I, $-C_{1-6}$alkyl, $-C_{1-6}$-alkenyl, $-C_{1-6}$-alkoxy, $-NO_2$, $-CN$, $-CF_3$, $-OCF_3$, $-C_{1-6}$-alkoxycarbonyl, $-SO_2-C_{1-6}$alkyl or $-SO_2$-aryl, or $R^6$ are each independently $-C_{1-20}$-alkyl, $-C_{3-8}$-cycloalkyl, aryl or heteroaryl, wherein aryl or heteroaryl are both optionally substituted by one or more group selected from each independently F, Cl, Br, I, $-C_{1-6}$-alkyl, $-C_{1-6}$-alkoxy, $-NO_2$, $-CN$, $-CF_3$, $-OCF_3$, or $-C_{1-6}$-alkoxycarbonyl; or $R^4$, $R^5$ and $R^6$ are a group of formula 1' wherein:

$X^{1'}$ and $X^{2'}$ are anionic ligands;

$L^{1'}$ is a neutral ligand;

$R^{1'}$ is $-C_{1-20}$-alkyl, $-C_{1-20}$-haloalkyl, $-C_{3-8}$-cycloalkyl or $-C_{7-13}$-aralkyl;

$R^{2'}$ is H, $-C_{1-20}$-alkyl, $-C_{2-20}$-alkenyl, $-C_{2-20}$-alkynyl or aryl;

$R^{3'}$ is $-C_{1-6}$alkyl, $-C_{1-6}$-alkoxy, aryl, F or Cl; and n' is 0, 1, 2 or 3

The compounds of formula 1 of the present invention may be used to catalyse olefin metathesis reactions including, but not limited to, ring opening metathesis polymerisation (ROMP), ring closing metathesis (RCM), depolymerisation of unsaturated polymers, synthesis of telechelic polymers, ene-ine metathesis and olefin synthesis.

Another embodiment of the present invention relates to novel 2-alkoxy-5-styrene derivatives of formula 2, which are intermediates for the preparation of complexes 1, wherein:

wherein $R^1$, $R^2$, $R^3$, n and Z are defined as above and

$R^{12}$ is $-C_{1-4}$-alkyl;

m is 0, 1 or 2.

The partial formula represents an alkylene group in which one or both hydrogen atoms of the methylene group may be replaced by the group $R^{12}$. Accordingly it covers the following alkylene groups:

A further aspect of the invention is the preparation of novel 2-alkoxy-5-styrene derivatives of formula 2, wherein:

A substituted 2-hydroxy-5-benzaldehyde 3 is alkylated by a $R^1V$, wherein $R^1$ has the meaning given for formula 1 and V is a leaving group selected from halogen atoms, $C_{1-6}$-alkyl-S(O)—O—, $C_{1-6}$-fluoroalkyl-S(O)—O—, aryl-S(O)—O— or aryl-S(O)$_2$—O—.

The substituted 2-alkoxy-5-benzaldehyde of formula 4 is then treated with an olefination reagent of formula wherein $R^4$ and m has the meaning given for formula 2 and W is a leaving group suitable for olefination reactions; to yield formula 2, Compound 2 can then be reacted with a ruthenium complex of formula 5 to result in the ruthenium complex of the formula 1 in which $L^1$ and $L^2$ are neutral ligands; $R^{13}$ is H, —$C_{1\text{-}20}$-alkyl, —$C_{2\text{-}20}$-alkenyl, —$C_{2\text{-}20}$-alkynyl or aryl; $R^{14}$ is aryl, vinyl or allenyl and X and X' are anionic ligands.

Optionally, the obtained compound of formula 1 can then be reacted with a different neutral ligand $L^1$ to replace the neutral ligand $L^1$ that is present in the compound of formula 1 and thereby obtain a different compound of formula 1.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins can also be present in the compounds described herein, and all such stable isomers are contemplated in the present invention. Cis and Trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

DETAILED DESCRIPTION OF THE INVENTION

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_{1\text{-}6}$ alkyl means an alkyl group or radical having 1 to 6 carbon atoms. Unless otherwise specified below, conventional definitions of terms control and conventional stable atom valences are presumed and achieved in all formulas and groups.

The term "optionally substituted" as used herein, means that any one or more hydrogens on the designated atom is replaced with a selection from the indicated group, provided that the designated atom's normal valence is not exceeded, and that the substitution results in a stable compound.

The term "aryl" as used herein, either alone or in combination with another substituent, means either an aromatic monocarbocyclic system or aromatic multicarbocyclic systems. For example, aryl includes a phenyl or a naphthyl ring system.

The term "heteroaryl" as used herein, either alone or in combination with another substituent, means a monovalent substituent derived by removal of a hydrogen, especially if a the annelated connection noted, then it means a divalent substituent derived by removal of two hydrogen, from a five-, six-, or seven-membered saturated or unsaturated (including aromatic) heterocycle containing carbon atoms and from one to four ring heteroatoms selected from nitrogen, oxygen and sulphur. Examples of suitable heterocycles include: tetrahydrofuran, thiophene, diazepine, isoxazole, piperidine, dioxane, morpholine, pyrimidine or The term "heteroaryl" also includes a heterocycle as defined above fused to one or more other cycle be it a heterocycle or any other cycle. One such examples includes indole or thiazolo[4,5-b]-pyridine. Although generally covered under the term "Heteroaromatic ring", the term "heteroaryl" as used herein precisely defines an unsaturated heterocycle for which the double bonds form an aromatic system. Suitable example of heteroaromatic system include: quinoline, indole, pyridine, The term "halogen" as used herein means a halogen substituent selected from fluoro, chloro, bromo or iodo.

The term "—$C_{1\text{-}20}$-alkyl" as used herein, either alone or in combination with another substituents, means acyclic, straight or branched chain alkyl substituents containing from one to twenty carbon atoms. The term "—$C_{1\text{-}6}$-alkyl" as used herein has the same meaning as the above mentioned term but contains less carbon atoms, precisely a maximum of six carbon atoms and is therefore preferred. The terms —$C_{1-20}$-alkyl or —$C_{1-6}$-alkyl can include i.e. methyl, ethyl, propyl, butyl, hexyl, 1-methylethyl, 1-methylpropyl, 2-methylpropyl or 1,1-dimethylethyl.

The term "—$C_{2-20}$-alkenyl" as used herein, either alone or in combination with another substituent, means acyclic, straight or branched chain alkenyl substituents containing from two to twenty carbon atoms and at least one double bond. The term "—$C_{2-6}$-alkenyl" as used herein has the same meaning as the above mentioned term but contains less carbon atoms, precisely a maximum of six carbon atoms and is therefore preferred. The terms —$C_{1-20}$-alkenyl or —$C_{1-6}$-alkenyl can include i.e. vinyl or allenyl.

The term "—$C_{2-20}$-alkynyl" as used herein, either alone or in combination with another substituent, means acyclic, straight or branched chain alkynyl substituents containing from two to twenty carbon atoms and at least one triple bond. The term "—$C_{2-6}$-alkynyl" as used herein has the same meaning then the above mentioned term but contains less carbon atoms, precisely a maximum of six carbon atoms and is therefore preferred.

The term "—$C_{3-8}$-cycloalkyl" as used herein, either alone or in combination with another substituent, means a cycloalkyl substituent containing five or six carbon atoms and includes i.e. cyclopentyl or cyclohexyl.

The term "—$C_{1-6}$-alkoxy" as used herein, either alone or in combination with another substituent, means the substituent —$C_{1-6}$-alkyl-O— wherein alkyl is as defined above containing up to six carbon atoms. Alkoxy includes methoxy, ethoxy, propoxy, 1-methyl-ethoxy, butoxy or 1,1-dimethylethoxy.

The term "—$C_{7-13}$-aralkyl" as used herein, either alone or in combination with another substituent, means the substituent -Aryl-$C_{1-6}$-alkyl- wherein alkyl is as defined above containing up to six carbon atoms. Aralkyl includes benzyl, phenylethyl, phenylpropyl, 1-phenyl-1-methylethyl or phenylbutyl.

The term "—$C_{1-20}$-haloalkyl" as used herein, either alone or in combination with another substituent, means acyclic, straight or branched chain alkyl substituents containing up to twenty carbon atoms having one or more hydrogens substituted for a halogen selected from bromo, chloro, fluoro or iodo. Preferably the term —$C_{1-20}$-haloalkyl represents —$C_{1-8}$-fluoroalkyl. The term "—$C_{1-8}$-fluoroalkyl" as used herein, either alone or in combination with another substituent, means acyclic, straight or branched chain alkyl substituents containing up to six carbon atoms having one or more hydrogens substituted by a flour atom such as 2-fluorethyl or 2,2,2-trifluorethyl. Preferably the terms —$C_{1-20}$-haloalkyl and —$C_{1-8}$-fluoroalkyl represent —$C_{1-6}$-perflouroalkyl such as trifluoromethyl or pentafluoroethyl.

Additional Embodiments

Preferred are compounds of general formula 1, wherein
$R^4$ is —$C_{1-20}$-alkyl or —$C_{3-8}$-cycloalkyl, both optionally substituted by one or more group selected from each independently F, Cl, Br, I or —$C_{1-6}$-alkoxycarbonyl, or aryl or heteroaryl both optionally substituted by one or more group selected from each independently F, Cl, Br, I, —$C_{1-6}$alkyl, —$C_{1-6}$-alkoxy, —$NO_2$, —CN, —$CF_3$, —$OCF_3$ or —$C_{1-6}$-alkoxycarbonyl
$R^5$ is —$C_{1-8}$-fluoroalkyl, aryl or heteroaryl, wherein aryl or heteroaryl are both optionally substituted by one or more groups selected from each independently F, Cl, Br, I, —$C_{1-6}$-alkyl, —$C_{1-6}$-alkenyl, —$C_{1-6}$-alkoxy, —$NO_2$, —CN, —$CF_3$, —$OCF_3$, —$C_{1-6}$-alkoxycarbonyl, —$SO_2$—$C_{1-6}$-alkyl, —$SO_2$-aryl or a group of formula 1';

$R^6$ are each independently —$C_{1-20}$-alkyl, —$C_{3-8}$-cycloalkyl, aryl or heteroaryl, wherein aryl or heteroaryl are both optionally substituted by one or more group selected from each independently F, Cl, Br, I, —$C_{1-6}$-alkyl, —$C_{1-6}$-alkoxy, —$NO_2$, —CN, —$CF_3$, —$OCF_3$, or —$C_{1-6}$-alkoxycarbonyl.

Also preferred are compounds of general formula 1, wherein
Z is —CO—$R^4$ or —PO($R^6$)$_2$; and
$R^4$ and $R^6$ are a group of formula 1'.

Preferred are compounds of formula 1a, wherein $L^1$, $X^1$, $X^2$, $R^1$, $R^2$, $R^3$, Z and n are defined as above.

1a

More preferred are the above mentioned compounds of general formula 1 or 1a wherein
$L^1$ is P($R^{11}$)$_3$ and $R^{11}$ are each independently —$C_{1-6}$-alkyl, —$C_{3-8}$-cycloalkyl or aryl; or
$L^1$ is a ligand of formula 6a, 6b, 6c or 6d,

6a

6b

6c

6d wherein
$R^7$ and $R^8$ are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen; particularly
$R^9$ and $R^{10}$ are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen or $R^9$ and $R^{10}$ together with the carbon atoms to which they are attached are combined to form a carbocyclic 3 to 8 membered ring.

Y and Y' are halogen.

Particularly preferred are compounds wherein $R^7$ and $R^8$ are each independently H, —$C_{1-6}$-alkyl, —$C_{2-6}$-alkenyl or phenyl, wherein the phenyl is optionally substituted with up to three groups independently selected from —$C_{1-6}$alkyl, —$C_{1-6}$-alkoxy or halogen;

$R^9$ and $R^{10}$ are each independently H, —$C_{1-6}$-alkyl, —$C_{2-6}$-alkenyl or phenyl, wherein the phenyl is optionally substituted with up to three groups independently selected from —$C_{1-6}$-alkyl, —$C_{1-6}$-alkoxy or halogen or $R^9$ and $R^{10}$ together with the carbon atoms to which they are attached are combined to form a carbocyclic 5 to 7 membered ring.

Most preferred are compounds of general formula 1 or 1a, wherein $R^1$ is iso-propyl;

$R^2$ is H, —$C_{1-6}$-alkyl or aryl, in particular H;

$X^1$ and $X'^2$ are halogen, particularly chlorine;

$L^1$ is P(cyclohexyl)$_3$ or $L^1$ is a group of formula 6a, 6b, 6c or 6d, more preferred a group of formula 6a;

6a wherein $R^7$ and $R^8$ are each 2,4,6-trimethylphenyl; and $R^9$ and $R^{10}$ are each H.

$R^7$ and $R^8$ are 2-methylbenzene, 2,6-dimethylbenzene or 2,4,6-trimethylbenzene;

n is 0.

In particular most preferred are compounds of general formula 1 or 1a, wherein $R^1$ is a iso-propyl;

$R^2$ is H;

$X^1$ and $X'^2$ are chlorine;

$L^1$ is a group of formula 6a;

6a wherein $R^7$ and $R^8$ are each 2,4,6-trimethypheny and $R^9$ and $R^{10}$ are each H;

$R^7$ and $R^8$ are 2-methylbenzene, 2,6-dimethylbenzene or 2,4,6-trimethylbenzene;

n is 0.

Preferred compounds of formula 2 are compounds of formula 2a, wherein $R^1$, $R^2$, $R^3$, $R^{12}$, Z, m and n are defined as above.

2a

More preferred are compounds of general formula 2 or 2a, wherein $R^1$ is a isopropyl group; and/or $R^2$ is H, —$C_{1-6}$-alkyl or aryl, in particular $R^2$ has the meaning of a hydrogen atom; and/or $R^{12}$ is —$C_{1-6}$-alkyl, in particular methyl or ethyl; and/or n is 0 and/or m is 0.

Additional embodiments are compounds of formula 2 or 2a wherein:

$R^1$ is iso-propyl;

$R^2$ is H;

m is 0; and n is 0.

Furthermore preferred is a process for manufacturing complexes of formula 1 or 1a, wherein a compound of general formula 2 or 2a, is reacted with a ruthenium complex of formula 5

5 wherein $L^1$ and $L^2$ are neutral ligands $R^{13}$ is H, —$C_{1-20}$-alkyl, —$C_{2-20}$-alkenyl, —$C_{2-20}$-alkynyl or aryl; and $R^{14}$ is aryl, vinyl or allenyl; and $X^1$ and $X'^2$ are anionic ligands;

optionally in the presence of a different neutral ligand $L^1$.

More preferred is the above mentioned synthesis of a ruthenium complex of formula 1, when the process is carried out:

in the presence of a copper salt, in particular CuCl; and/or in a halogenated or an aromatic solvent, particularly selected from methylene chloride, chloroform, benzene, toluene, xylene, mesitylene or mixtures thereof; and/or at a temperature from 0 to 100° C., in particular at a temperature from 10 to 80° C., more particular at a temperature from 20 to 60° C.; and/or in a time period from 1 to 24 h, in particular 1 to 10 h, more particular 1 to 4 h.

Most preferred is the above mentioned synthesis of a ruthenium complex, wherein the reaction is carried out in one vessel by mixing the ligand of formula 6a, 6b, 6c or 6d with a solid complex of formula 5, wherein both ligands $L^1$ and $L^2$ are phosphines of formula P($R^{11}$)$_3$, wherein $R^{11}$ has the meaning as above and thereafter adding a ligand of formula 2 or 2a.

One preferred variation of the above mentioned synthesis of a ruthenium complex is the generation of the ligands of general formula 6a, 6b, 6c or 6d in situ from the stable salts of the formulae 7a, 7b, 7c or 7d, wherein the anion is selected from formiate, acetate, trifluoro-acetate or another acid group, a halogen or $[BF_4]^-$. Therefore, the salt is preferably in form of a suspension in solvents such as aliphatic or aromatic hydrocarbons, preferably hexane, reacted with a strong base, selected from alkali metal hydrides, alkaline earth metal hydrides or alcoholates, particularly potassium tert-pentanolate, potassium tert-amylate or potassium tert-butanolate. Thereafter reaction is continued by adding a solid complex of formula 5, wherein both ligands $L^1$ and $L^2$ are phosphines of formula $P(R_{11})_3$ and thereafter adding a ligand of formula 2 or 2a, to yield a compound of general formula 1 or 1a.

Moreover preferred is a process for manufacturing intermediates, which comprises the steps of a) alkylating a compound of general formula 3, with a reagent of formula $R^1V$ (9) to form a intermediate of formula 4, and b) reacting 4 with an olefination reagent of formula 10 to yield a compound of the general formula 2, wherein $R^1$, $R^2$, $R^3$, $R^{12}$, Z, m and n of formula 2a, 3, 4, 9 and 10 are defined as above and W is a leaving group suitable for olefination reactions; and V is halogen, —$C_{1-6}$alkyl-S(O)—O—, —$C_{1-6}$-fluoroalkyl-S(O)—O—, aryl-S(O)—O— or aryl-S(O)$_2$—O—.

More preferred is a process, wherein the above mentioned step a) is carried out:

in an aprotic solvent, in particular selected from DMF, DMSO, acetone, acetonitrile, ethyl acetate, glycol ether, methanol, ethanol or mixtures thereof, more particular the solvent is DMF; or in a biphasic solvent system fitted with a phase transfer catalyst; or in presence of a catalyst, in particular the catalyst is selected from $Cs_2CO_2$, CsF, quaternary ammonium salts, crown ethers or cryptands, more particular $Cs_2CO_3$; or in the presence of an alkali metal carbonate or an alkali hydroxide, in particular selected from $Na_2CO_3$, $K_2CO_3$, $Li_2CO_3$, $Cs_2CO_3$, NaOH, KOH, LiOH, CsOH; or in a time period from 1 to 24 h, in particular 8 to 24 h, more particular 16 to 24 h.

at a temperature from 0 to 150° C., in particular at a temperature from 10 to 100° C., more particular at a temperature from 20 to 80° C.; or Starting from compound 4, compound 2 is available under Tebbe, Wittig, Wittig-Horner, Wittig-Horner-Emmons or Peterson conditions, but preferred is a process, wherein the above mentioned step b) is carried out:

in a solvent selected from alcohols, glycol ethers or cyclic ethers, preferred is THF; or W is a leaving group suitable for olefination reactions according to Tebbe, with Tebbe's titanium reagent, or according to Wittig, with Wiltig's phosphonium ylide reagent, more particular a leaving group selected from $PPh_3$ or $TiCp_2$; wherein Ph is substituted or unsubstituted phenyl and Cp is a substituted or unsubstituted cyclopentadienyl-anion, which can be found after reaction in its oxidised form.

Another preferred embodiment of the invention is a process for metathesis reactions of all types, comprising contacting an olefin with a catalyst of general formula 1; in particular wherein the metathesis reaction is a ring closing or cross metathesis reaction.

The following examples are to illustrate various embodiments of the present invention and are not to be understood as limiting the present invention in a way.

EXAMPLE 1 a) 4-Methoxy-benzene-phosphonic-acid-diethylester is prepared in analogy to Chem. Ber. (1970) 103, 2428–2436.
b) 4-Methoxy-benzene-phosphonic-acid-diethylester (1.3 g, 12.3 mmole), $SOCl_2$ (14.6 g, 123 mmole), and DMF (0.9 ml) are heated to reflux under argon for 4 hours. After removal of remaining $SOCl_2$ under vacuum, 2.4 g crude 4-Methoxy-benzene-phosphonic-acid-dichloride is obtained.
c) 10.8 g 4-Brom-chlorbenzene is reacted with 1.38 g magnesium in 100 ml THF to Grignard reagent. The resulting mixture is added under argon over 40 minutes to a cooled solution (−78° C.) of 4-Methoxy-benzenephosphonic-acid-dichloride (2.42 g) and THF (60 ml). Thereafter the mixture is stirred for 10 h at room temperature. A saturated $NH_4Cl$ solution is added and the solvent removed under vacuum. The residue is threatened with 100 ml $CH_2Cl_2$, filtered through silica gel and dried again. Product is purified by column chromatography (hexane/ethyl acetate, 4:2). 2.15 g of pure 4-Methoxyphenyl-bis(4-chlorophenyl)-phosphinoxid is obtained.
$m_p$: 106–107° C.
d) 4-Methoxyphenyl-bis(4-chlorophenyl)-phosphinoxid (1.84 g, 4.88 mmole) and $CH_2Cl_2$ (30 ml) are cooled to −78° C. $BBr_3$ (1.84 g, 7.32 mmole) is added and the resulting mixture is stirred for 26 h at r.t. $H_2O$ (30 ml) is added and $CH_2Cl_2$ removed under stirring at 80° C. After 6 h the mixture is cooled down and the product precipices. Solid residue is purified by column chromatography (methanol/ethyl acetate/$H_2O$, 5:50:0.5). 1.26 g of pure 4-Hydroxyphenyl-bis(4-chlorophenyl)-phosphinoxid is obtained.
$m_p$: 116–119° C.

EXAMPLE 2 a) $K_2CO_3$ (298 mg, 2.2 mmole), $Cs_2CO_3$ (104 mg, 0.32 mmole) and 8 ($R^{6'}$=p-Cl-phenyl, 400 mg, 1.1 mmole) are placed in a flask. DMF (5.5 ml) is added and the mixture is stirred about 5 minutes. After the time, allyl bromide (190 µl, 2.2 mmole) is added and the mixture is stirred for another 24 h at 35° C. DMF is evaporated under vacuum, water (10 ml) is added and the mixture is extracted with ethyl acetate (3×25 ml). Combined extracts are dried and evaporated to dryness. 440 mg (99%) of crude 9 ($R^{6'}$=p-Cl-phenyl) is obtained.

$^1$H NMR (400 MHz, $CDCl_3$): δ=4.59 (dt, J=5.4, J=1.5 Hz, 2H), 5.30–5.34 (m, 1H), 5.39–5.45 (m, 1H); 6.00–6.09 (m, 1H), 6.98–7.01 (m, 2H), 7.43–7.47 (m, 4H), 7.50–7.62 (m, 6H).

b) A solution of 9 ($R^{6'}$=p-Cl-phenyl, 400 mg, 1.0 mmole) in 1,2,4-trichlorobenzene (5 ml) is heated under Argon at 200–210 C for 8 h. After cooling, n-pentane (ca. 40 ml) is added and a light-brown solid is formed, which is filtered-off and dried. 337 mg of crude 10 ($R^{6'}$=p-Cl-phenyl) is obtained.

$^1$H NMR (400 MHz, $CD_3OD$): δ=3.30–3.32 (m, 2H), 4.96–4.98 (m, 1H), 4.99–5.02 (m, 1H), 5.87–5.97 (m, 1H) 6.90–6.93 (m, 1H), 7.23–7.29 (m, 1H), 7.31–7.36 (m, 1H), 7.54–7.62 (m, 8H)

c) 10 ($R^{6'}$=p-Cl-phenyl, 300 mg; 0.75 mmole), $RhCl_3 \cdot 3H_2O$ (19 mg, 0.075 mmole, 10% mol) and p-toluene sulfonic acid (14 mg, 0.075 mmole, 10% mol) are placed in a flask. EtOH (5 ml) and $H_2O$ (0.5 ml) are added and the mixture is refluxed under Argon for 5 h. A dark red solution is formed. $H_2O$ (10 ml) is added and ethanol was evaporated. The mixture is extracted with $CH_2Cl_2$ (5×15 ml), the combined extracts are washed with water, dried and filtered. The filtrate is evaporated. 294 mg (99%) of 11 ($R^{6'}$=p-Cl-phenyl) is obtained.

$^1$H NMR (400 MHz, $CDCl_3$): 1.80 (dd, J=6.6, J=1.6 Hz, 3H), 6.01–6.11 (m, 1H), 6.57 (d, J=16.0 Hz, 1H), 6.92–6.96 (m, 1H), 7.14–7.20 (m, 1H), 7.36–7.46 (m, 4H), 7.53–7.59 (m, 5H)

d) $K_2CO_3$ (182 mg, 1.3 mmole), $Cs_2CO_3$ (83 mg, 0.26 mmole), and 11 ($R^{6'}$=p-Cl-phenyl, 270 mg, 0.67 mmole) are placed in flask. DMF (3.0 ml) is added and the mixture is stirred about 5 min. Thereafter, isopropyl iodide (150 µl, 1.5 mmole) is added and the mixture is stirred for 22 h at 35° C. $H_2O$ (6 ml) is added and the mixture is extracted with ethyl acetate (3×15 ml). Combined extracts are dried and evaporated to dryness. Product is purified by column chromatography (ethyl acetate/cyclohexane, 1:1). 155 mg (52%) of pure 12 ($R^{6'}$=p-Cl-phenyl) is obtained.

13C NMR (100 MHz, CDCl₃): δ=19.0, 21.9, 70.6, 112.8 (d, J=13 Hz), 121.2, 122.3, 124.8, 128.0, 128.8 (d, J=13 Hz), 130.3, 130.7, 131.7, 133.3 (d, J=11 Hz), 138.6, 157.7

EXAMPLE 3

A solution of t-Butyl lithium (0.8 mmole) in 5 ml of Et₂O is dropped slowly to a solution of 11' (0.4 mmole, 96.5 mg) in 2 ml THF, at −78° C. 15 min later PO(R⁶')₂ (R⁶'=phenyl, 0.8 mmole, 189.3 mg) in 10 ml of THF is added slowly. The reaction mixture is stirred for 30 min at −78° C. an then allowed under stirring to warm up to room temperature within 3 h. Aqueous, saturated NH₄Cl (6 ml) is added, the THF removed and the residue extracted with CH₂Cl₂ (3×10 ml). The combined organic layers are washed with water, dried with anhydrous MgSO₄, filtered and concentrated. The residue is purified by flash chromatography (50% EtOAc in cyclohexane).

13C-NMR (125 MHz, CDCl₃) δ=22.0, 70.7, 112.8 (d, J=13.4 Hz), 115.6, 127.5 (d,. J=11.8 Hz). 127.7 (d, J=18.9 Hz), 128.4 (d, J=19 Hz), 131.1.

EXAMPLE 4 a) A solution of t-Butyl lithium (0.8 mmole) in 5 ml of Et₂O is dropped slowly to a solution of 11' (0.4 mmole, 96.5 mg) in 2 ml THF, at −78° C. 15 min later 13 (0.8 mmole, 84.9 mg) in 10 ml of THF is added slowly. The reaction mixture is stirred for 30 min at −78° C. an then allowed under stirring to warm up to room temperature overnight. Aqueous, saturated NH₄Cl (6 ml) is added, the THF removed and the residue extracted with CH₂Cl₂ (3×10 ml). The combined organic layers are washed with water, dried with anhydrous MgSO₄, filtered and concentrated. The residue is purified by flash chromatography (5% EtOAc in cyclohexane).

13C-NMR (125 MHz, CDCl₃) δ=22.2, 71.0, 76.0, 114.1, 114.3, 125.0, 126.5, 127.0, 127.4, 127.8, 128.4, 131.9, 135.9, 143.9, 154.7.

b) 14 (0.4 mmole, 0.1 g) was dissolved in 15 ml CH₂Cl₂, Pyridinium chromate (0.48 mmole, 103.4 mg) was added slowly and the resulting mixture was stirred at room temperature for 1 h. The solvent was removed and the residue purified by flash chromatography (5% EtOAc in cyclohexane).

13C-NMR (125 MHz, CDCl₃) δ=22.1, 70.8, 112.2, 115.4, 127.3, 128.2, 129.3, 129.6, 129.7, 131.2, 131.6, 131.8, 138.3, 158.7, 195.6.

EXAMPLE 5

Second generation Grubb's catalyst 16 (Mes=mesityl, 153 mg, 0.18 mmole) and CuCl (31 mg, 0.31 mmole) are placed in Schlock's flask. CH₂Cl₂ (3 ml) is added under Argon and a solution of 12 (R⁶'=p-Cl-phenyl, 86 mg, 0.19 mmole;) in CH₂Cl₂ (6 ml) is added. The solution is stirred at 40° C. for 40 min under Argon. CuCl (10 mg) is added and the mixture is stirred for 1 h. Thereafter solvent is evaporated, ethyl acetate (ca. 20 ml) is added, solid residues are filtered off and the filtrate is concentrated under vacuum. The product is purified by column chromatography (ethyl acetate/cyclohexane, 1:1). The product 1b (R⁶'=p-Cl-phenyl, 131 mg, 81%) is obtained as a green solid.

LRMS (ESI, MeOH and CH$_2$Cl$_2$): 896.1 (M$^+$). HRMS (ESI, MeOH and CH$_2$Cl$_2$): calcd. for C$_{43}$H$_{45}$O$_2$N$_2$$^{35}$Cl$_3$$^{102}$Ru (M$^+$–Cl): 859.1322. found 859.1358.

EXAMPLE 6 a) A solution of 17 (500 mg) in 1,2,4-trichlorobenzene (8 ml) is heated at 210 C for 6 h. After cooling, hexane (ca.80 ml) is added and 12 hours later a solid product is formed, which is filtered-off and dried. After chromatography (hexane/ethyl acetate, 3:2) 383 mg of the product 18 is obtained.

b) 18 (165 mg; 0.5 mmole), RhCl$_3$.3H$_2$O (13.1 mg, 0.05 mmole, 10% mol) and p-toluene sulfonic acid (6.8 mg, 0.05 mmole, 10% mol) are placed in flask. EtOH (4.5 ml) and H$_2$O (0.5 ml) are added and the mixture is refluxed for 3 h. The mixture is evaporated to dryness, ethyl acetate is added and then filtered over 5 g of silica gel. The filtrate is evaporated. 157 mg of the product 19 is obtained.

c) A solution of 19 (440 mg) in 1,2,4-trichlorobenzene (7 ml) is heated at 210 C for 6 h. After cooling, hexane (ca.80 ml) is added and 12 hours later a solid product is formed, which is filtered-off and dried. After chromatography (hexane/ethyl acetate, 3:2) 258 g of the product 20 is obtained.

m$_p$: 147–148° C.

d) 20 (258 mg; 0.75 mmole), RhCl$_3$.3H$_2$O (19 mg, 0.075 mmole, 10% mol) and p-toluene sulfonic acid (0.014 g, 0.075 mmole, 10% mol) are placed in flask. EtOH (4.5 ml) and H$_2$O (0.5 ml) are added and the mixture is refluxed for 3 h. The mixture is evaporated to dryness, ethyl acetate added and then filtered over 5 g of silica gel. The filtrate is evaporated. 235 mg of the product 21 is obtained.

EXAMPLE 7

Second generation Grubb's catalyst 16 (Mes=mesityl, 140 mg, 0.166 mmole) and CuCl (20 mg, 0.20 mmole) are placed in Schlock's flask. CH$_2$Cl$_2$ (4 ml) is added under Argon and then a solution of 21 (56 mg, 0.165 mmole) in CH$_2$Cl$_2$ (5 ml) is added. The solution is stirred at 40° C. for 50 min under Argon. Thereafter, solvent is evaporated, ethyl acetate (ca. 10 ml) is added, white solid is filtered off and the filtrate is concentrated under vacuum. The product is puri- fied by column chromatography (15%–30% ethyl acetate in cyclohexane). The product 1f (80 mg, 60%) is obtained as a green solid.

EXAMPLE 8

Analogously to the processes described in the examples 1 to 7, the following compounds of formula 1c, 1d, 1e, 1g and 1h are obtained. For instance, according to example 5 compound 12' is a ligand for complex 1c, compound 15 for complex 1d or according to example 4 and 5 heptanone can be reacted with 11', oxidised and reacted with 16 to obtain complex 1e.

EXAMPLE 9

Figure 1:
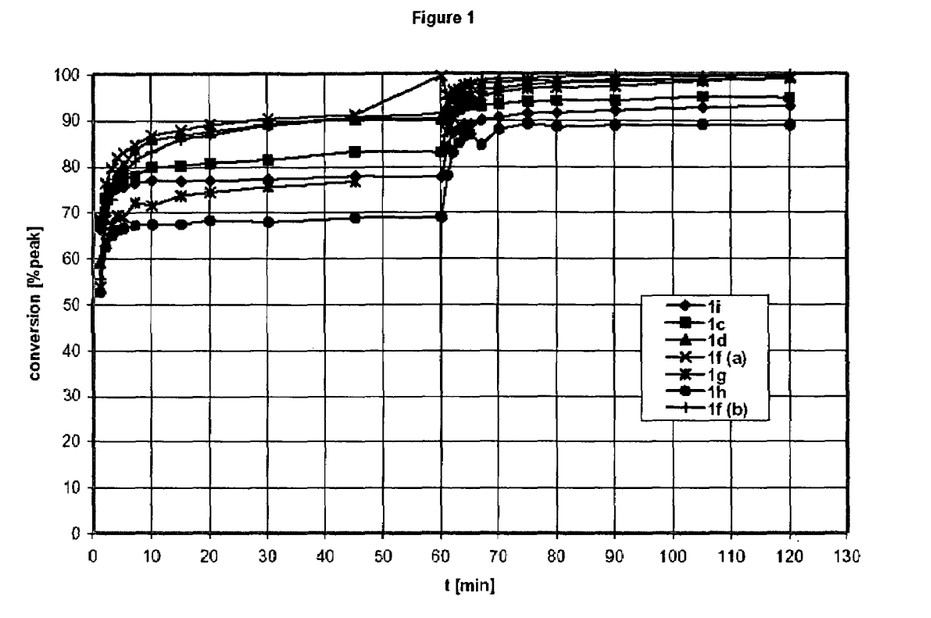
FIG. 1 is a graph comparing the cyclisation speed of 22 when using a ruthenium catalyst according to the present invention versus using a known ruthenium catalyst 1i (see Example 9).

Toluene is degassed by bubbling through nitrogen, 22 is dissolved in 10 ml of degassed toluene and added into the reaction flask. The solution is heated up to 80° C. and freshly prepared catalysts 1c–h is added ($1^{st}$) under nitrogen. After stirring for 60 min at the same temperature the conversion is checked by HPLC. A second amount of catalysts 1c–h ($2^{nd}$) is added under nitrogen and the conversion is checked 60 min later a second time by HPLC. FIG. 1 is a graph comparing the cyclisation speed of 22. Table 1 shows the results of the HPLC analysis, wherein the catalyst 1c–h are compared with a known catalyst of formula 1i (*Angew. Chem. Int. Ed.* 2002, 41, 4038).

TABLE 1

| catalyst | 1st [mol %] 2nd [mol %] | 22 [mol] | toluene [ml] | conversion [% Peak at 200 nm] 23 [60 min] 23 [120 min] | 22 [60 min] 22 [120 min] |
|---|---|---|---|---|---|
| 1c | 0.4 | 0.0075 | 554 | 66.4 | 33.6 |
|  | 0.2 |  |  | 96.2 | 3.8 |
| 1d | 0.4 | 0.0075 | 554 | 80.1 | 19.9 |
|  | 0.2 |  |  | 96.9 | 3.1 |
| 1e | 0.4 | 0.0075 | 554 | 89.9 | 10.1 |
|  | 0.2 |  |  | 98.9 | 1.1 |
| 1f (1st run) | 0.4 | 0.0075 | 554 | 99.3 | 0.7 |
|  | 0.2 |  |  | 99.1 | 0.9 |
| 1f (2nd run) | 0.4 | 0.0025 | 185 | 91.3 | 8.7 |
|  | 0.2 |  |  | 99.5 | 0.5 |
| 1g | 0.2 | 0.0075 | 554 | — | — |
|  | 0.1 |  |  | 98.8 | 1.2 |
| 1h | 0.4 | 0.0075 | 554 | 68.7 | 31.3 |
|  | 0.2 |  |  | 88.7 | 11.3 |
| 1i | 0.4 | 0.0075 | 554 | — | — |
|  | 0.2 |  |  | 96.5 | 3.5 |
| 1i | 0.4 | 0.015 | 1008 | 77.4 | 22.6 |
|  | 0.2 |  |  | 92.8 | 7.2 |

EXAMPLE 10

23.5 g Tetrakis hydroxy methyl phosphonium chloride (80%, 98.7 mmole) is dissolved in isopropanole (35 ml) under a nitrogen atmosphere. Then 12.1 g (98.7 mmole) of a 45% KOH solution is added within 5 min while the solution is cooled (temperature 20–25° C.). After stirring the suspension for another 30 min under nitrogen, the mixture is filtered and the inorganic residue is washed with 20 ml of degassed isopropanole. The combined isopropanole solution is stored under a nitrogen atmosphere until use.

After cooling to 60° C. 2.3 g (2.8 mmole) of the trihydroxy methyl phosphine (THP) solution is added to the reaction mixture of example 13. After stirring for 5 h at 60° C. the mixture is cooled to room temperature and extracted twice with 40 ml of degassed water, 40 ml of 0.5 M HCl, 40 ml of 0.5 M NaHCO$_3$ solution, and 40 ml of water. Approx. 695 ml of toluene are distilled of at 50° C. in vacuum (150 mbar) and the residue is treated at 50° C. with 1.4 g of charcoal. The remaining liquid is added to 210 ml of pre-cooled methyl cyclohexane (5° C.). After stirring for further 60 min at 5° C. the precipitate is filtered and washed with 100 ml of methyl cyclohexane (twice). The white solid is dried in vacuum at 30° C. to yield 23 as an almost white powder.

| catalyst | total yield | % of 23 | % of 22 |
|---|---|---|---|
| 1c | 96.2 | 86.02 | 1.20 |
| 1d | 94.3 | 85.44 | 1.95 |

We claim:

1. A compound of formula 1, wherein:
$X^1$ and $X^2$ are anionic ligands;
$L^1$ is a neutral ligand;
$R^1$ is —$C_{1-20}$-alkyl, —$C_{1-20}$-haloalkyl, —$C_{3-8}$-cycloalkyl or —$C_{7-13}$-aralkyl;
$R^2$ is H, —$C_{1-20}$-alkyl, —$C_{2-20}$-alkenyl, —$C_{2-20}$-alkynyl or aryl;
$R^3$ is —$C_{1-6}$alkyl, —$C_{1-6}$-alkoxy, aryl, F or Cl;
n is 0, 1, 2 or 3;
Z is —CO—$R^4$, —$SO_2$—$R^5$ or —PO($R^6$)$_2$;
$R^4$ is —$C_{1-20}$-alkyl or —$C_{3-8}$-cycloalkyl, both optionally substituted by one or more groups each independently selected from F, Cl, Br, I or —$C_{1-6}$alkoxycarbonyl, or aryl or heteroaryl both optionally substituted by one or more group selected from each independently F, Cl, Br, I, —$C_{1-6}$-alkyl, —$C_{1-6}$alkoxy, —$NO_2$, —CN, —$CF_3$, —$OCF_3$ or —$C_{1-6}$-alkoxycarbonyl;
$R^5$ is —$C_{1-8}$-fluoroalkyl, aryl or heteroaryl, wherein aryl or heteroaryl are both optionally substituted by one or more groups each independently selected from F, Cl, Br, I, —C$_{1-6}$-alkyl, —C$_{1-6}$alkenyl, —C$_{1-6}$-alkoxy, —NO$_2$, —CN, —CF$_3$, —OCF$_3$, —C$_{1-6}$-alkoxycarbonyl, —SO$_2$—C$_{1-6}$-alkyl or —SO$_2$-aryl; and R$^6$ are each independently —C$_{1-20}$-alkyl, —C$_{3-8}$-cycloalkyl, aryl or heteroaryl, wherein aryl or heteroaryl are both optionally substituted by one or more group each independently selected from F, Cl, Br, I, —C$_{1-6}$alkyl, —C$_{1-6}$alkoxy, —NO$_2$, —CN, —CF$_3$, —OCF$_3$, or —C$_{1-6}$-alkoxycarbonyl; or R$^4$, R$^5$ and R$^6$ are each independently a group of formula 1' wherein
X$^{1'}$ and X$^{2'}$ are anionic ligands;
L$^{1'}$ is a neutral ligand;
R$^{1'}$ is —C$_{1-20}$-alkyl, —C$_{1-20}$-haloalkyl, —C$_{3-8}$-cycloalkyl or —C$_{7-13}$-aralkyl;
R$^{2'}$ is H, —C$_{1-20}$-alkyl, —C$_{2-20}$-alkenyl, —C$_{2-20}$-alkynyl or aryl;
R$^{3'}$ is —C$_{1-6}$alkyl, —C$_{1-6}$-alkoxy, aryl, F or Cl; and
n' is 0, 1, 2 or 3.

2. A compound of formula 1, according to claim 1, wherein
R$^4$ is —C$_{1-20}$-alkyl or —C$_{3-8}$-cycloalkyl, both optionally substituted by one or more group each independently selected from F, Cl, Br, I or —C$_{1-6}$alkoxycarbonyl, or aryl or heteroaryl both optionally substituted by one or more group selected from each independently F, Cl, Br, I, —C$_{1-6}$-alkyl, —C$_{1-6}$-alkoxy, —NO$_2$, —CN, —CF$_3$, —OCF$_3$ or —C$_{1-6}$alkoxycarbonyl;
R$^5$ is —C$_{1-8}$-fluoroalkyl, aryl or heteroaryl, wherein aryl or heteroaryl are both optionally substituted by one or more groups each independently selected from F, Cl, Br, I, —C$_{1-6}$-alkyl, —C$_{1-6}$-alkenyl, —C$_{1-6}$-alkoxy, —NO$_2$, —CN, —CF$_3$, —OCF$_3$, —C$_{1-6}$alkoxycarbonyl, —SO$_2$—C$_{1-6}$-alkyl, —SO$_2$-aryl or a group of formula 1'; and
R$^6$ are each independently —C$_{1-20}$-alkyl, —C$_{3-8}$-cycloalkyl, aryl or heteroaryl, wherein aryl or heteroaryl are both optionally substituted by one or more group each independently selected from F, Cl, Br, I, —C$_{1-6}$-alkyl, —C$_{1-6}$alkoxy, —NO$_2$, —CN, —CF$_3$, —OCF$_3$, or —C$_{1-6}$-alkoxycarbonyl.

3. A compound of formula 1, according to claim 1, wherein
Z is —CO—R$^4$ or —PO(R$^6$)$_2$; and
R$^4$ and R$^6$ are a group of formula 1'.

4. A compound of formula 1, according to claim 1, wherein
R$_1$ is —C$_{1-6}$-alkyl, —C$_{1-6}$-haloalkyl, —C$_{3-8}$-cycloalkyl or —C$_{7-13}$-aralkyl;
R$^2$ is H, —C$_{1-6}$-alkyl, —C$_{2-6}$-alkenyl, —C$_{2-6}$-alkynyl or aryl;
R$^3$ is —C$_{1-6}$-alkyl, —C$_{1-6}$-alkoxy, aryl, F or Cl;
Z is —CO—R$^4$, —SO$_2$—R$^5$ or —PO(R$^6$)$_2$;

R$^4$ is —C$_{1-6}$-alkyl or —C$_{3-8}$-cycloalkyl, both optionally substituted by one or more group each independently selected from F, Cl, Br, I or —C$_{1-6}$-alkoxycarbonyl, or aryl or heteroaryl both optionally substituted by one or more group selected from each independently F, Cl, Br, I, —C$_{1-6}$-alkyl, —C$_{1-6}$-alkoxy, —NO$_2$, —CN, —CF$_3$, —OCF$_3$ or —C$_{1-6}$-alkoxycarbonyl;
R$^5$ is —C$_{1-8}$-fluoroalkyl, aryl or heteroaryl, wherein aryl or heteroaryl are both optionally substituted by one or more group each independently selected from F, Cl, Br, I, —C$_{1-6}$-alkyl, —C$_{1-6}$-alkenyl, —C$_{1-6}$-alkoxy, —NO$_2$, —CN, —CF$_3$, —OCF$_3$, —C$_{1-6}$-alkoxycarbonyl, —SO$_2$—C$_{1-6}$-alkyl or —SO$_2$-aryl; and
R$^6$ are each independently —C$_{1-6}$-alkyl, —C$_{3-8}$-cycloalkyl, aryl or heteroaryl, wherein aryl or heteroaryl are both optionally substituted by one or more group each independently selected from F, Cl, Br, I, —C$_{1-6}$-alkyl, —C$_{1-6}$-alkoxy, —NO$_2$, —CN, —CF$_3$, —OCF$_3$, or —C$_{1-6}$-alkoxycarbonyl; or
R$^4$, R$^5$ and R$^6$ are each independently a group of formula 1' wherein:
X$^{1'}$ and X$^{2'}$ are anionic ligands;
L$^{1'}$ is a neutral ligand;
R$^{1'}$ is —C$_{1-6}$-alkyl, —C$_{1-6}$-haloalkyl, —C$_{3-8}$-cycloalkyl or —C$_{7-13}$-aralkyl;
R$^{2'}$ is H, —C$_{1-6}$-alkyl, —C$_{2-6}$-alkenyl, —C$_{2-6}$-alkynyl or aryl;
R$^{3'}$ is —C$_{1-6}$alkyl, —C$_{1-6}$-alkoxy, aryl, F or Cl; and
n' is 0, 1, 2 or 3.

5. A compound of formula 1a, wherein X$^1$, X$^2$, L$^1$ R$^1$, R$^2$, R$^3$, n, and Z are as defined in claim 1.

6. A compound according to claim 1, wherein
X$^1$ and X$^2$ each independently are F, Cl, Br or I.

7. A compound according to claim 1, wherein
X$^1$ and X$^2$ are Cl.

8. A compound according to claim 1, wherein
Z is —CO—R$^4$, —SO$_2$—R$^5$ or —PO(R$^6$)$_2$;
R$^4$ is aryl or heteroaryl both optionally substituted by one or more group each independently selected from F, Cl, Br, I, —$C_{1-6}$alkyl, —$C_{1-6}$-alkoxy, —$NO_2$, —CN, —$CF_3$, —$OCF_3$ or —$C_{1-6}$-alkoxycarbonyl;

$R^5$ is aryl or heteroaryl, both optionally substituted by one or more group each independently selected from F, Cl, Br, I, —$C_{1-6}$alkyl, —$C_{1-6}$-alkenyl, —$C_{1-6}$alkoxy, —$NO_2$, —CN, —$CF_3$, —$OCF_3$, —$C_{1-6}$-alkoxycarbonyl, —$SO_2$—$C_{1-6}$-alkyl, —$SO_2$-aryl or a group of formula 1'; and $R^6$ are each independently —$C_{1-6}$alkyl, —$C_{3-8}$-cycloalkyl, aryl or heteroaryl, wherein aryl or heteroaryl are both optionally substituted by one or more group each independently selected from F, Cl, Br, I, —$C_{1-6}$alkyl, —$C_{1-6}$alkoxy, —$NO_2$, —CN, —$CF_3$, —$OCF_3$, or —$C_{1-6}$-alkoxycarbonyl.

9. A compound according to claim 1, wherein
Z is —CO—$R^4$, —$SO_2$—$R^5$ or —PO($R^6$)$_2$;
$R^4$ is aryl optionally substituted by one or more group each independently selected from F, —$C_{1-6}$alkoxy, —$NO_2$ or —$CF_3$;
$R^5$ is aryl optionally substituted by one or more group each independently selected from F, —$C_{1-6}$alkoxy, —$NO_2$, —$CF_3$, —$SO_2$—$C_{1-6}$-alkyl or —$SO_2$-aryl; and
$R^6$ are aryl, both optionally substituted by one or more group each independently selected from F, —$C_{1-6}$ alkoxy, —$NO_2$ or —$CF_3$.

10. A compound according to claim 1, wherein
n is 0.

11. A compound according to claim 1, wherein
$R^1$ is iso-propyl.

12. A compound according to claim 1, wherein
$R^2$ is H or —$CH_3$.

13. A compound according to claim 1, wherein:
$L^1$ is P($R^{11}$)$_3$ or a ligand of formula 6a, 6b, 6c or 6d:

$R^{11}$ is —$C_{1-6}$alkyl, —$C_{3-8}$-cycloalkyl or aryl;
$R^7$ and $R^8$ are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen;
$R^9$ and $R^{10}$ are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen; or

$R^9$ and $R^{10}$ together with the carbon atoms to which they are attached are combined to form a carbocyclic 3 to 8 membered ring; and

Y and Y' are halogen.

14. A compound according to claim 1, wherein:
$L^1$ is P($R^{11}$)$_3$ or a ligand of formula 6a, 6b, 6c or 6d:

$R^{11}$ is —$C_{1-6}$alkyl, —$C_{3-8}$-cycloalkyl or aryl;
$R^7$ and $R^8$ are each independently H, —$C_{1-6}$-alkyl, —$C_{2-6}$-alkenyl or phenyl, wherein the phenyl is optionally substituted with up to three groups independently selected from —$C_{1-6}$alkyl, —$C_{1-6}$-alkoxy or halogen;
$R^9$ and $R^{10}$ are each independently H, —$C_{1-6}$-alkyl, —$C_{2-6}$-alkenyl or phenyl, wherein the phenyl is optionally substituted with up to three groups independently selected from —$C_{1-6}$-alkyl, —$C_{1-6}$-alkoxy or halogen; or
$R^9$ and $R^{10}$ together with the carbon atoms to which they are attached are combined to form a carbocyclic 3 to 8 membered ring; and

Y and Y' are halogen.

15. A compound according to claim 1, wherein
$L^1$ is a ligand of formula 6a, 6b, 6c or 6d,
$R^7$ and $R^8$ are each independently tolyl, m-xylyl or mesityl; and
$R^9$ and $R^{10}$ are each independently H or —$C_{1-6}$-alkyl.

16. A compound according to one of the claim 1, wherein:
$L^1$ is P($R^{11}$)$_3$; and
$R^{11}$ is phenyl or cyclohexyl.

17. A compound selected from formulas 1b–1h:

1b

1c

1d

1e

1f

1g

1h wherein Mes is mesityl, Ph is phenyl and p-Cl-Ph is para-chlorphenyl.

18. A process for manufacturing a compound of formula 1 according to claim 1, said process comprising reacting a compound of formula 2:

2 wherein $R^1$, $R^2$, $R^3$, n and Z are defined as in claim 1;
$R^{12}$ is —$C_{1-4}$-alkyl; and
m is 0, 1 or 2;
with a ruthenium complex of formula 5:

5 wherein
$X^1$, $X^2$ and $L^1$ are as defined in claim 1;
$L^2$ is a neutral ligand, wherein $L^2$ must not be the same group as $L^1$ at the same time;
$R^{13}$ is H, —$C_{1-20}$-alkyl, —$C_{2-20}$-alkenyl, —$C_{2-20}$-alkynyl or aryl; and
$R^{14}$ is aryl, vinyl or allenyl.

19. A process for manufacturing a compound of formula 1a according to claim 5, said process comprising reacting a compound of formula 2a:

wherein
$R^1$, $R^2$, $R^3$, n and Z are defined as in claim 5;
$R^{12}$ is —$C_{1-4}$-alkyl; and
m is 0, 1 or 2;
with a ruthenium complex of formula 5:

wherein
$X^1$, $X^2$ and $L^1$ are as defined in claim 5;
$L^2$ is a neutral ligand, wherein $L^2$ must not be the same group then $L^1$ at the same time;
$R^{13}$ is H, —$C_{1-20}$-alkyl, —$C_{2-20}$-alkenyl, —$C_{2-20}$-alkynyl or aryl; and
$R^{14}$ is aryl, vinyl or allenyl.

20. A process for carrying out a metathesis reaction, comprising contacting two compounds each having a C=C double bond, or one compound having at least two C=C double bonds, with a catalyst, wherein the catalyst is a compound according to claim 1.

21. A process for carrying out a ring closing or cross metathesis reaction which process comprises contacting a dialkenyl compound with a compound according to claim 1.

* * * * *